US008377704B2

(12) United States Patent
DiMagno et al.

(10) Patent No.: US 8,377,704 B2
(45) Date of Patent: Feb. 19, 2013

(54) DETECTION AND QUANTIFICATION OF ANIONS

(75) Inventors: Stephen DiMagno, Lincoln, NE (US); Ronald Cerny, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 186 days.

(21) Appl. No.: 12/907,079

(22) Filed: Oct. 19, 2010

(65) Prior Publication Data

US 2011/0091982 A1 Apr. 21, 2011

Related U.S. Application Data

(60) Provisional application No. 61/253,124, filed on Oct. 20, 2009.

(51) Int. Cl.
*G01N 33/00* (2006.01)
*G01N 33/15* (2006.01)
*B01D 59/44* (2006.01)

(52) U.S. Cl. .......... 436/124; 436/57; 436/100; 436/101; 436/106; 436/109; 436/110; 436/127; 436/129; 436/173

(58) Field of Classification Search ............. 436/57, 436/100–101, 106, 109–110, 124, 127, 129, 436/173
See application file for complete search history.

(56) References Cited

U.S. PATENT DOCUMENTS

| 2005/0226776 | A1* | 10/2005 | Brady et al. ............... 422/99 |
| 2006/0120958 | A1 | 6/2006 | Brady et al. |
| 2006/0128031 | A1* | 6/2006 | Robotti et al. ............. 436/518 |
| 2006/0292060 | A1* | 12/2006 | Wadsworth et al. ......... 423/500 |
| 2007/0092441 | A1 | 4/2007 | Wadsworth et al. |
| 2009/0286992 | A1* | 11/2009 | Carroll et al. .............. 548/527 |
| 2011/0091982 | A1 | 4/2011 | DiMagno et al. |
| 2011/0144344 | A1* | 6/2011 | Woodcraft ................ 546/180 |
| 2011/0190505 | A1 | 8/2011 | DiMagno |
| 2011/0313170 | A1 | 12/2011 | DiMagno |
| 2012/0004417 | A1 | 1/2012 | DiMagno |

FOREIGN PATENT DOCUMENTS

| WO | WO 03/002157 | 1/2003 |
| WO | WO 2005/061415 | 7/2005 |
| WO | WO 2005/097713 | 10/2005 |
| WO | WO 2008/082695 | 7/2008 |
| WO | WO 2010/008522 | 1/2010 |
| WO | WO 2010/048170 | 4/2010 |

OTHER PUBLICATIONS

Pike, V. W. et al, Journal of the Chemical Society, Chemical Communications 1995, 2215-2216.*
Shah, A. et al, Journal of the Chemical Society, Perkins Transactions I 1998, 2043-2046.*
Ermert, J. et al, Journal of Labelled Compounds & Radiopharmaceuticals 2004, 47, 429-441.*
Ross, T. L. et al, Journal of the American Chemical Society 2007, 129, 8018-8025.*
Abboud et al., "Hydrogen Bonding in the Gas Phase and in Solution. New Experimental Developments," *Quantitative Treatments of Solute/Solvent Interactions*, Polarizer and Murray Ed. Elsevier: Amsterdam, 1994, pp. 134-179.
Adams et al., "Nucleophilic routes to selectively fluorinated aromatics," *Chem. Soc. Rev.*, 1999, 28:225-231.

(Continued)

*Primary Examiner* — Arlen Soderquist
(74) *Attorney, Agent, or Firm* — Fish & Richardson P.C.

(57) ABSTRACT

Provided herein are methods of detecting anions in solution. In particular, the methods can be used to detect trace anions in solution. For example, the anions can be present in an amount of between about 500 femtomoles to about 10 millimoles.

29 Claims, 2 Drawing Sheets

OTHER PUBLICATIONS

Albrecht et al., "Structural Versatility of Anion—πInteractions in Halide Salts with Pentafluorophenyl Substituted Cations," *J. Am. Chem. Soc.*, 2008, 130:4600-01.

Al-Qahtani et al., "Palladium(II)-mediated 11C-carbonylative coupling of diaryliodonium salts with organostannanes. A new, mild and rapid synthesis of aryl [11C]ketones," *J. of Chem Soc. Perkin Transactions 1*, 2000, 1033-1036.

Bailly et al., "Pentafluorophenyliodine(III) compounds. Part 3. (Pentafluorophenyl)iodine difluoride: alternative preparations, molecular structure, and properties," *Z. Anorg. Allg. Chem.*, 2000, 626:1406-1413.

Bielawski et al., "High-yielding one-pot synthesis of diaryliodonium triflates from arenes and iodine or aryl iodides," *Chem. Commun.*, 2007, 2521-2523.

Biffinger et al., "The Polar Hydrophobicity of Fluorinated Compounds," *ChemBioChem*, 2004, 5:622-627.

Bini et al., "Development of Cation/Anion 'Interaction' Scales for Ionic Liquids through ESI-MS Measurements," *J. Phys. Chem. B*, 2007, 111(3):598-604.

Blondel et al., "Electron spectrometry at the μeV level and the electron affinities of Si and F," *J. Phys. B: At., Mol. Opt. Phys.*, 2001, 34:2757.

Boechat et al., "Fluorodenitrations using tetramethylammonium fluoride," *J. Chem. Soc., Chem. Commun.*, 1993, 921-922.

Cai et al., "Chemistry with [18F]fluoride ion," *European Journal of Organic Chemistry*, 2008, 17:2853-2873.

Cerioni et al., "Solution structure of bis(acetoxy)iodoarenes as observed by $^{17}$O NMR spectroscopy," *Tetrahedron Lett.*, 2004, 45:505-507.

Choudhury et al., "Crystal engineering via C-H F and C-H π interactions in two substituted indoles," *Acta Cryst.*, 2004, C60:o644.

Christe et al., "Quantitative Measure for the 'Nakedness' of Fluoride Ion Sources," *J. Am. Chem. Soc.*, 2003, 125:9457-9461.

Christe et al., "Syntheses, properties, and structures of anhydrous tetramethylammonium fluoride and its 1:1 adduct and trans-3-amino-2-butenenitrile," *J. Am. Chem. Soc.*, 1990, 112:7619-25.

Ciufolini et al., "Oxidative adaption of phenols through the use of hypervalent iodine reagents" *Development and applications. Synthesis*, 2007, 3759-3772.

Crivello, "A new visible light sensitive photinitiator system for the cationic polymerization of epoxides," *J. Polym. Sci., Part A: Polym. Chem.*, 2009, 47:866-875.

Crivello, "Photoactivated cationic ring-opening frontal polymerization of oxetanes," Designed monomers and polymers 2005, 8, 517-531.

Curran, D. P. et al. "Experimental techniques in fluorous synthesis: A user's guide," *Comb. Chem.*, 2000, 327-352.

Darses et al., "Potassium organotrifluoroborates. New partners in palladium-catalyzed cross-coupling reactions," *Eur. J. Org. Chem.*, 1999, 1875-1883.

Darses et al., "Potassium trifluoro(organo)borates: New perspectives in organic chemistry," *Eur. J. Org. Chem.*, 2003, 4313-4327.

Davies et al., "Ab initio and DFT computer studies of complexes of quaternary nitrogen cations: trimethylammonium, tetramethylammonium, trimethylethylammonium, choline and acetylcholine with hydroxide, fluoride and chloride anions," *Phys. Chem. Chem. Phys.*, 2003, 5:4533-4540.

DiMagno et al., "Facile Synthesis of meso-Tetrakis(perfluoroalkyl)porphyrins: Spectroscopic Properties and X-ray Crystal Structure of Highly Electron-Deficient 5,10,15,20-Tetrakis(heptafluoroproyl)porphyrin," *J. Org. Chem.*, 1994, 59:6943.

DiMagno et al., "The Strength of Weak Interactions: Aromatic Fluorine in Drug Design," *Curr. Top. Med. Chem.*, 2006, 6:1473-1482.

Dohi et al., "A chiral hypervalent iodine(III) reagent for enantioselective dearomatization of phenols," *Angew. Chem. Int. Ed. Engl*, 2008, 47,:3787-90.

Fernandez et al., "Multinuclear PG SE Diffusion and Overhauser NMR Studies on a Variety of Salts in THF Solution," *Inorg. Chem.*, 2005, 44:5509-5513.

Frohn et al., "Preparation of polyfluorinated cycloalk-1-enyl-, alk-1-enyl-, and alkyliodine tetrafluorides using XeF2 in the presence of appropriate Lewis acids as fluorooxidant," *J. Fluorine Chem.*, 2005, 126:1036-1043.

Giroldo et al., "An Unusually Fast Nucleophilic Aromatic Displacement Reaction: The Gas-Phase Reaction of Fluoride Ions with Nitrobenzene," *Angew Chem. Int. Ed.*, 2004, 43:3588-3590.

Gnann et al., "Naked Fluoride Ion Sources: Synthesis, Characterization, and Coupling Reaction of 1-Methylhexamethylenetetramine Fluoride," *J. Am. Chem. Soc.*, 1997, 119:112-115.

Grushin et al., "Arylation of anions with diarylhalonium fluoroborates under conditions of interphase catalysis," *Bulletin of the Academy of Sciences of the UUSR. Division of Chemical Science, Consultants Bureau*, 1984, 33(10):2130-2135.

Hansch et al., "A survey of Hammett substituent constants and resonance and field parameters," *Chem. Rev.*, 1991, 91(2):165-195.

Hof et al., "A Weak Attractive Interaction between organic Fluorine and an Amide Group," *Angew. Chem. Int. Ed.*, 2004, 43:5056-5059.

Hossain et al., "Reaction of iodoarenes with potassium peroxodisulfate/trifluoroacetic acid in the presence of aromatics. Direct preparation of diaryliodonium triflates from iodoarenes," *Tetrahedron*, 2006, 62:6955-6960.

Huang et al., "Synthesis of ether-linked fluorocarbon surfactants and their aggregational properties in organic solvents," *Journal of Colloid and Interface Science*, 2004, 272:457-464.

Kang et al., "Palladium-catalyzed coupling and carbonylative coupling of silyoxy compounds with hypervalent iodonium salts," *Tetrahedron Lett.*, 1997, 38:1947-1950.

Kang et al., "Palladium-Catalyzed Cross-Coupling of Organoboron Compounds with Iodonium Salts and Iodanes," *J. Org. Chem.*, 1996, 61:4720-4724.

Kazmierczak et al., "A simple, two-step conversion of various iodo arenes to (diacetoxyiodo) arenes with chromium(VI) oxide as the oxidant," *Synthesis*, 1998, 1721-1723.

Kazmierczak et al., "Syntheses of (diacetoxyiodo)arenes or iodylarenes from iodoarenes, with sodium periodate as the oxidant," *Molecules*, 2001, 6:881-891.

Ko et al., "Fluorous-Based Carbohydrate Microarrays," *J. Am. Chem. Soc.* 2005, 127, 13162-13163.

Kornath et al., "Tetramethylphosphonium Fluoride: 'Naked' Fluoride and Phosphorane," *Inorg. Chem.*, 2003, 42:2894-2901.

Kraszkiewicz et al., "Facile syntheses of symmetrical diaryliodonium salts from various arenes, with sodium metaperiodate as the coupling reagent in acidic media," *Synthesis*, 2008, 2373-2380.

Lubinkowski et al., "Reactions of diaryliodonium fluoroborates with inorganic anions," *J. Org. Chem.*, 1978, 2432-2435.

Lummis et al., "A Caton-π Binding Interaction with a Tyrosine in the Binding Site of the GABA Receptor," *Chemistry & Biology*, 2005, 12:993-997.

McMillen et al., "Hydrocarbon Bond Dissociation Energies," *Ann. Rev. Phys. Chem.*, 1982, 33:493 (abstract only).

McKillop et al., "Further functional-group oxidations using sodium perborate," *Tetrahedron*, 1989, 45:3299-306

Merritt et al., "Diaryliodonium Salts: A Journey from Obscurity to Fame," *Angew. Chem., Int. Ed.*, 2009, 48:9052-9070.

Moore et al., "Hypervalent iodine-promoted phenolic oxidations: Generation of a highly versatile o-quinone template," *Chemtracts*, 2002, 15:74-80.

Moriarty et al., "Oxidation of phenolic compounds with organohypervalent iodine reagents," *Org. React.*, 2001, 57:327-415.

Okuyama et al., "Solvolysis of Cyclohexenyliodonium Salt, a New Precursor for the Vinyl Cation: Remarkable Nucleofugality of the Phenyliodonio Group and Evidence for Internal Return from an Intimate Ion-Molecule Pair," *J. Am. Chem. Soc.*, 1995, 117:3360-7.

Olsen et al., "A Fluorine Scan of Thrombin Inhibitors to Map the Fluorophilicity/Fluorophobicity of an Enzyme Active Site: Evidence for CF•••C¼OInteractions," *Angew Chem.*, 2003, 115:2611.

Padelidakis et al., "Synthesis and characterization of 2,6-difluorophenyliodine(III) derivatives," *J. Fluorine Chem.*, 1999, 99:9-15.

Page et al., "Simple direct synthesis of [bis(trifluoroacetoxy)iodo]arenes," *Synthesis*, 2006, 3153-3155.

Pearson et al., "Nucleophilic reactivity constants toward methyl iodide and trans-dichlorodi (pyridine)platinum(II)," *J. Am. Chem. Soc.*, 1968, 90:319-326.

Plenio et al., "The Coordination Chemistry of Fluorocarbons: Difluoro-m-cyclophane-Based Flurorcryptands and Their Group I and II Metal Ion Complexes," *Inorg. Chem.*, 1997, 36:5722.

Quideau et al., "Chemical and electrochemical oxidative activation of arenol derivatives for carbon-carbon bond formation," *Curr. Org. Chem.*, 2004, 8:113-148.

Ryan et al., "Direct α-arylation of ketones: the reaction f cyclic ketone enolates with diphenyliodonium triflate," *Tetrahedron Lett.*, 1997, 38:5061-5064.

Sánchez et al., "Regioselective functionalisation of nitrobenzene and benzonitrile derivatives via nucleophilic aromatic substitution of hydrogen by phosphorus-stabilized carbanions," *Tetrahedron*, 2006, 62:3648-3662.

Schwesinger et al., "Stable Phosphazenium Ions in Synthesis—an Easily Accessible, Extremely Reactive 'Naked' Fluoride Salt," *Angew. Chem. Int. Ed. Engl.*, 1991. 30:1372.

Seppelt, "Does the Naked Fluoride Ion Exist?" *Angew. Chem., Int. Ed. Engl.*, 1992, 31:292.

Sharefkin et al., "Iodosobenzene Diacetate," *Org. Synth*, 1963, 43, No pp. given.

Stoyanov et al., "An Infrared vNH Scale for Weakly Basic Anions. Implications for Single-Molecule Acidity and Superacidity," *J. Am. Chem. Soc.*, 2006, 128:8500-8508.

Sun et al., "A Method for Detecting Water in Organic Solvents," *Org. Lett.*, 2008, 10:4413-4416.

Sun et al., "Anhydrous Tetrabutylammonium Fluoride," *J. Am. Chem. Soc.*, 2005, 127:2050-2051.

Sun et al., "Competitive demethylation and substitution in N,N,N-trimethylanilinium fluorides," *J. Fluor. Chem.*, 2007, 128:806-812.

Sun et al., "Fluoride relay: a new concept for the rapid preparation of anhydrous nucleophilic fluoride salts from KF," *Chem. Commun.*, 2007, 528-529.

Sun et al., "Room-Temperature Nucleophilic Aromatic Fluorination: Experimental and Theoretical Studies," *Angew. Chem. Int. Ed.*, 2006, 45:2720-2725.

Sun et al., "Rapid Preparation of Fluorinated Aromatic Heterocycles," *ACS symposium series*, 2009, 1003:85-104.

Thalladi et al., "C-H•••F Interactions in the Crystal Structures of Some Fluorobenzenes," *J. Am. Chem. Soc.*, 1998, 120:8702-8710.

Thayer, "Fabulous Fluorine: Having fluorine in life sciences molecules brings desirable benefits, but the trick is getting it in place and making south-after building blocks," *C&E News*, 2006, 84:15-24.

Toba, "The design of photoinitiator systems," *J. Photopolym. Sci. Technol.*, 2003, 16:115-118.

Tohma et al., "Preparation and reactivity of 1,3,5,7-tetrakis[4-(diacetoxyiodo)phenyl]adamantane, a recyclable hypervalent iodine(III) reagent," *Angew. Chem., Int. Ed.*, 2004, 43:3595-3598.

Tsuzuki et al., "Magnitude and orientation dependence of intermolecular interaction between perfluoroalkanes: High level *ab initio* calculations of $CF_4$ and $C_2F_6$ dimers," *J. Chem. Phys.*, 2002, 116:3309-3315.

Tsuzuki et al., "Magnitude and orientation dependence of intermolecular interaction of perfluoropropane dimer studied by high-level ab initio calculations: comparison with propane dimer," *J. Chem. Phys.*, 2004, 121: 9917-9924.

Tsuzuki et al., "Magnitude of Interaction between n-Alkane Chains and Its Anisotropy: High-Level ab Initio Calculations of n-Butane, n-Petane, and n-Hexane Dimers," *J. Phys. Chem. A*, 2004, 108:10311-10316.

Uyanik et al., "Enantioselective Kita Oxidative Spirolactonization Catalyzed by In Situ Generated Chiral Hypervalent Iodine (III) Species," *Angew. Chem., Int. Ed.*, 2010, 49, 2175-2177, S2175/1-S2175/79.

Van Der Puy et al., "Conversion of diaryliodonium salts to aryl fluorides," *Journal of Fluorine Chemistry*, 1982, 21:385-392.

Wenthold et al., "Bond Dissociation Energies of $F_2^-$ and $HF_2^-$. A Gas-Phase Experimental and 62 Theoretical Study," *J. Phys. Chem.*, 1995, 99:2002-2005.

Ye et al., "Straightforward Syntheses of Hypervalent Iodine (III) Reagents Mediated by Selectfluor," *Org. Lett.*, 2005, 7:3961-3964.

Zhan et al., "Hydration of the Fluoride Anion: Structures and Absolute Hydration Free Energy from the First-Principles Electronic Structure Calculations," *J. Phys. Chem. A*, 2004, 108, 2020-2029.

Zhang et al., "A practical route for synthesizing a PET ligand containing [$^{18}$F] fluorobenzene using reaction of diphenyliodonium salt with [$^{18}$F]F$^-$," *Tetrahedron Letters*, 2007, 48(49):8632-8635.

Zhang et al., "Diels-Alder reaction and double phenylation in reaction of thiophenes with diphenyliodonium triflate," *Heterocycles*, 2004, 64:199-206.

Zhdankin et al., "Chemistry of Polyvalent Iodine," *Chem. Rev.*, 2008, 108:5299-5358.

Zhong et al., "From ab initio quantum mechanics to molecular neurobiology: A cation-π binding site in the nicotinic receptor," *PNAS*, 1998, 95:12088-12093.

Zielinska et al., "Easy preparation of (diacetoxyiodo)arenes from iodoarenes with sodium percarbonate as the oxidant," *Molecules*, 2002, 7:806-809.

\* cited by examiner

DETECTION AND QUANTIFICATION OF ANIONS

CROSS-REFERENCE TO RELATED APPLICATIONS

This application claims benefit under 35 U.S.C. 119(e) to U.S. Application No. 61/253,124, filed on Oct. 20, 2009.

FEDERALLY SPONSORED RESEARCH OR DEVELOPMENT

The U.S. Government may have certain rights in this invention pursuant to Grant No. CHE-0717562 awarded by the National Science Foundation.

TECHNICAL FIELD

This disclosure relates to a method for detecting anions in a solution. In particular, the disclosure relates to a method for detecting trace anions suspected to be present in an amount of between 500 femtomoles and 10 millimoles.

BACKGROUND

Many applications require knowledge of the identity and concentration of trace anions in water or other solutions. For samples of limited volume, rapid, simultaneous identification and quantification of such anions becomes extraordinarily difficult as the background ion concentrations enter the part per billion (ppb) range. As the amount of the anion of interest decreases in the sample, the difficulty of detecting and quantifying the anion in solution increases. Many current techniques require the anion to be present in concentrations of at least a ppb for quantitative detection, but such concentrations can be unattainable in many applications (e.g., radiotracer synthesis). Additional difficulties arise when the anion of interest is in a sample with competing anions at similar or higher concentrations. In particular, detecting the presence and concentration of a specific anion of interest in the presence of other anions of similar reactivity can be difficult. For example, low concentrations of chloride ion may be precipitated from an aqueous solution using silver ion, but any bromide or fluoride ions present will also precipitate as insoluble silver bromide and silver fluoride salts.

As another example, determining the amount and purity of $^{18}F$ incorporated during the synthesis of positron emission tomography (PET) radiotracers can be difficult. Such detection problems arise because background $^{19}F$-fluoride ion concentrations in the $^{18}O$-labeled water target may substantially exceed the amount of $^{18}F$-labeled fluoride in the radiotracer sample. When the background concentration of $^{19}F$-fluoride ion is large, the synthesized radiotracer can be contaminated with the non-radioactive analogue. In such cases, the radiochemical purity and suitability of the radiotracer for PET imaging may be compromised.

SUMMARY

Provided herein are methods of detecting anions in solution. In particular, the methods described can be used to detect trace anions (i.e. anions present in an amount of between about 500 femtomole and 10 millimoles) in a sample. The methods described herein facilitate the detection of anions present at low concentrations and in the presence of high concentrations (e.g., one million fold excess) of other background ions. These methods are particularly useful for samples of limited volume, where rapid and simultaneous identification and quantification of an anion is desired, for example, in the production of PET radiotracers and in the analysis of water contaminants.

The sensitivity of the method is such that it requires only a small fraction (<10%) of the $^{18}O$-labeled water target, and enables pre-screening of the $^{18}F$ fluoride solution prior to radiotracer preparation. Since the target volume is normally on the order of one mL and the $^{18}F$-fluoride concentration is typically on the order of 1 nanomole/mL, the method is able to detect and quantify 1-2 ng of $^{18}F$-fluoride ion the presence of $^{19}F$-fluoride and other anionic contaminants. Moreover, the dynamic range is sufficient to quantify the $^{18}F/^{19}F$-fluoride ion ratio even in the presence of a large excess of $^{19}F$-fluoride ion.

Specifically, provided herein is a method of quantifying the amount of one or more anions, Y, in a sample. The method includes combining a compound of formula (I):

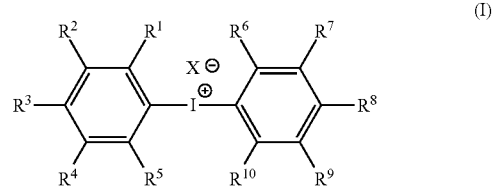

wherein:

$R^1$, $R^2$, $R^3$, $R^4$, $R^5$, $R^6$, $R^7$, $R^8$, $R^9$, $R^{10}$ are independently chosen from: H, —$(C_1$-$C_{10})$alkyl, —$(C_1$-$C_{10})$haloalkyl, $(C_2$-$C_{10})$alkenyl, $(C_2$-$C_{10})$alkynyl, —O—$(C_1$-$C_{10})$alkyl, halogen, —C=O—O—$(C_1$-$C_{10})$alkyl, aryl, heteroaryl, or a linking group that is bound either covalently or noncovalently to a solid support; and X is a weakly coordinating anion;

with a sample comprising one or more anions, Y, in a solvent, to prepare a compound of formula (II):

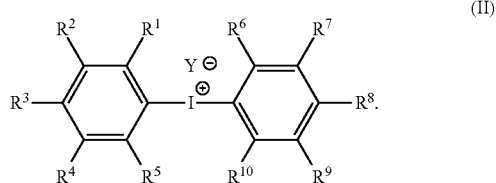

The compound of formula (II) can then be decomposed to form an aromatic compound of formula (III) and/or (IV):

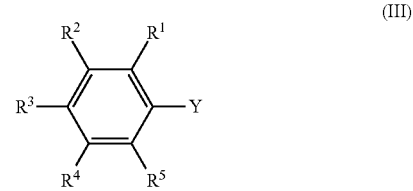

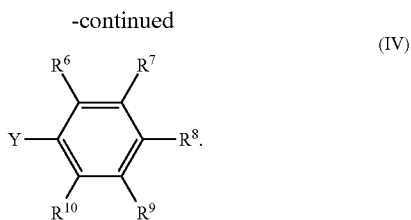

This sample can then be analyzed using mass spectroscopy to quantify the amount of the compound of formula (III) and/or (IV), thereby quantifying the amount of anion Y.

In some embodiments, the compound of formula (I) is:

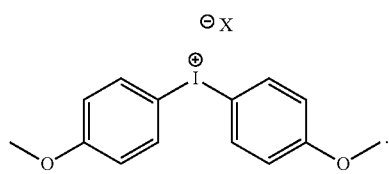

In some embodiments, the compound of formula (I) is in excess compared to Y.

In some embodiments, X can be chosen from: triflate, mesylate, nonaflate, hexaflate, toluene sulfonate, nitrophenyl sulfonate, bromophenyl sulfonate, tetraphenylborate, hexafluorophosphate, trifluoroacetate, tetrafluoroborate, and perchlorate.

In some embodiments, the pKa of the conjugate acid of Y is less than 12. For example, Y can be chosen from halide, aryl carboxylate, alkyl carboxylate, phosphate, phosphonate, phosphonite, azide, thiocyanate, cyanate, phenoxide, and mixtures thereof. In some embodiments, Y is chosen from fluoride, chloride, bromide, iodide, and azide. For example, Y can be fluoride; specifically, Y can be a radioactive isotope of fluoride. In some embodiments, Y is present in the sample in an amount from about 500 femtomoles to about 10 millimoles.

Decomposition can be performed through heating the sample at a temperature ranging from about 25° C. to about 250° C. The heating can be accomplished by a flash pyrolysis method, a conventional heating method, or by a microwave method. In some embodiments, the sample is heated from about 1 second to about 15 minutes.

In some embodiments, the compound of Formula I is supported on a solid support by means of either a covalently bound linking group, or by adsorption using noncovalent interactions.

In some embodiments, the solvent is a polar organic solvent. For example, the polar organic solvent can be chosen from acetonitrile, acetone, dichloromethane, ethyl acetate, tetrahydrofuran, dimethylformamide, 1,2-difluorobenzene, benzotrifluoride and mixtures thereof. In such cases, for example, the method further include removing the polar organic solvent; and dissolving the remaining sample in a nonpolar organic solvent prior to decomposing. In some embodiments, the method further includes removing the polar organic solvent; dissolving the remaining sample in a nonpolar organic solvent; and removing residual salt by filtration prior to decomposing. The nonpolar organic solvent can be, for example, benzene, toluene, o-xylene, diethyl ether, carbon tetrachloride, hexane, cyclohexane, fluorobenzene, chlorobenzene, nitrobenzene, or mixtures thereof.

In some embodiments, the anion can be present in the sample in an amount from about 500 femtomoles to about 1 millimole. For example, the anion can be present in the sample in an amount from about 500 femtomoles to about 1 micromole or from about 500 femtomoles to about 1 nanomole. In some embodiments, the anion is present in the sample in an amount of less than about 10 millimoles.

Analyzing the sample can include determining the amount of Y quantitatively. For example, analyzing can include determining the concentration of Y quantitatively. In some embodiments, analyzing includes determining the isotope ratio of Y, for example, the $^{18}F:^{19}F$ isotope ratio.

In some embodiments, the compound of formula (II) can be decomposed in the absence of solvent.

Further provided herein is a method of quantifying the amount of one or more anions, Y, in a sample wherein the method can include combining a compound of formula (I):

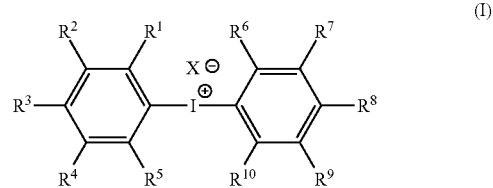

wherein:

$R^1$, $R^2$, $R^3$, $R^4$, $R^5$, $R^6$, $R^7$, $R^8$, $R^9$, $R^{10}$ are independently chosen from: H, —$(C_1$-$C_{10})$alkyl, —$(C_1$-$C_{10})$haloalkyl, $(C_2$-$C_{10})$alkenyl, $(C_2$-$C_{10})$alkynyl, —O—$(C_1$-$C_{10})$alkyl, halogen, —C=O—O—$(C_1$-$C_{10})$alkyl, aryl, and heteroaryl, or a linking group that is bound either covalently or noncovalently to a solid support; and X is a weakly coordinating anion;

with a sample comprising one or more anions, Y, in a polar organic solvent, to prepare a compound of formula (II):

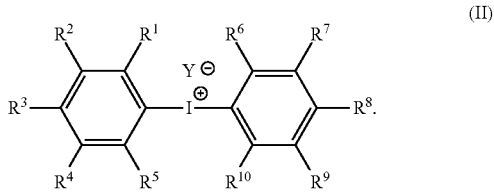

The method can further include removing the polar organic solvent, dissolving the remaining sample in a nonpolar organic solvent, and decomposing the compound of formula (II) to form an aromatic compound of formula (III) and/or (IV):

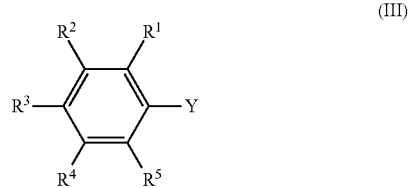

-continued

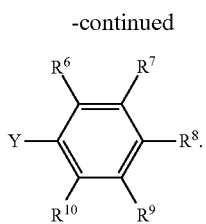
(IV)

The sample can then be analyzed using mass spectroscopy to quantify the amount of the compound of formula (III) and/or (IV), thereby quantifying the amount of anion Y.

A method of determining the presence or absence of one or more anions, Y, in a sample, is further provided herein, the method includes combining a sample with a compound of formula (I):

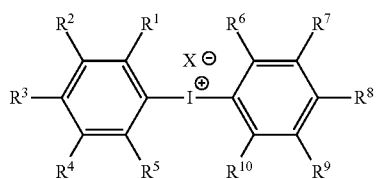
(I)

wherein:

$R^1$, $R^2$, $R^3$, $R^4$, $R^5$, $R^6$, $R^7$, $R^8$, $R^9$, $R^{10}$ are independently chosen from: H, —($C_1$-$C_{10}$)alkyl, —($C_1$-$C_{10}$)haloalkyl, ($C_2$-$C_{10}$)alkenyl, ($C_2$-$C_{10}$)alkynyl, —O—($C_1$-$C_{10}$)alkyl, halogen, —C=O—O—($C_1$-$C_{10}$)alkyl, aryl, and heteroaryl, or a linking group that is bound either covalently or noncovalently to a solid support; and X is a weakly coordinating anion; and analyzing the sample for the presence or absence of one or more anions, Y, using mass spectroscopy.

The details of one or more embodiments of the invention are set forth in the accompanying drawings and the description below. Other features, objects, and advantages of the invention will be apparent from the description and drawings, and from the claims.

DETAILED DESCRIPTION

Definitions

Figure 1:
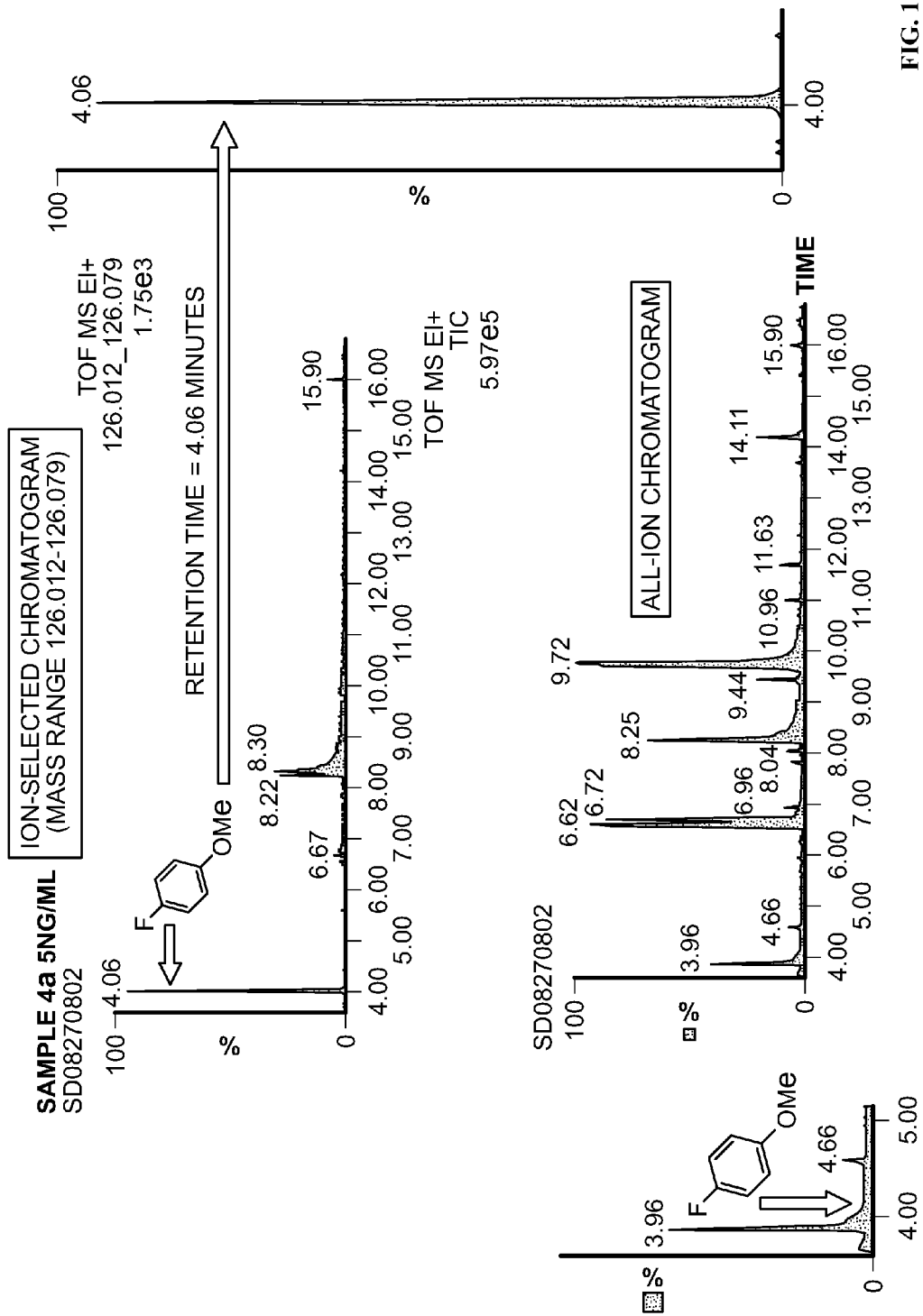
FIG. 1 illustrates an all-ion chromatogram and an ion-selected chromatogram of a solution containing trace amounts of fluoride following treatment with bis(4-methoxyphenyl)iodonium triflate.

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

Wherever the phrase "for example," "such as," and the like are used herein, the phrase "and without limitation" is understood to follow unless explicitly stated otherwise. As used herein, "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The term "alkyl" includes saturated aliphatic groups, including straight-chain alkyl groups (e.g., methyl, ethyl, propyl, butyl, pentyl, hexyl, heptyl, octyl, nonyl, and decyl) and branched-chain alkyl groups (isopropyl, tert-butyl, and isobutyl). The term alkyl further includes alkyl groups, which can further include oxygen, nitrogen, sulfur or phosphorus atoms replacing one or more carbons of the hydrocarbon backbone. In certain embodiments, a straight chain or branched chain alkyl has 6 or fewer carbon atoms in its backbone (e.g., $C_{1-6}$ for straight chain, $C_{3-6}$ for branched chain). The term $C_{1-6}$ includes alkyl groups containing 1 to 6 carbon atoms.

Moreover, the term "alkyl" includes both "unsubstituted alkyls" and "substituted alkyls," the latter of which refers to alkyl moieties having substituents replacing a hydrogen on one or more carbons of the hydrocarbon backbone. Such substituents can include, for example, alkyl, alkenyl, alkynyl, halogen, hydroxyl, carboxylate, alkoxyl, amino (including alkyl amino, dialkylamino, arylamino, diarylamino, and alkylarylamino), nitro, trichloromethyl, trifluoromethyl, or an aryl moiety.

The term "alkenyl" includes aliphatic groups that may or may not be substituted, as described above for alkyls, containing at least one double bond and at least two carbon atoms. For example, the term "alkenyl" includes straight-chain alkenyl groups (e.g., ethylenyl, propenyl, butenyl, pentenyl, hexenyl, heptenyl, octenyl, nonenyl, and decenyl) and branched-chain alkenyl groups. The term alkenyl further includes alkenyl groups that include oxygen, nitrogen, sulfur or phosphorus atoms replacing one or more carbons of the hydrocarbon backbone. In certain embodiments, a straight chain or branched chain alkenyl group has 6 or fewer carbon atoms in its backbone (e.g., $C_{2-6}$ for straight chain, $C_{3-6}$ for branched chain). The term $C_{2-6}$ includes alkenyl groups containing 2 to 6 carbon atoms.

The term "alkynyl" includes unsaturated aliphatic groups analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, and decynyl) and branched-chain alkynyl groups. The term alkynyl further includes alkynyl groups that include oxygen, nitrogen, sulfur or phosphorus atoms replacing one or more carbons of the hydrocarbon backbone. In certain embodiments, a straight chain or branched chain alkynyl group has 6 or fewer carbon atoms in its backbone (e.g., $C_{2-6}$ for straight chain, $C_{3-6}$ for branched chain). The term $C_{2-6}$ includes alkynyl groups containing 2 to 6 carbon atoms.

In general, the term "aryl" includes groups, including 5- and 6-membered single-ring aromatic groups (e.g., phenyl), alkyl substituted aryl groups, and aryl substituted alkyl groups. Furthermore, the term "aryl" includes polycyclic aryl groups, e.g., tricyclic, bicyclic, such as naphthalene. An aryl group may be substituted at one or more ring positions with substituents.

In general, the term "heteroaryl" includes groups, including 5- and 6-membered single-ring aromatic groups that include from one to four heteroatoms, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like.

The terms "halo" and "halogen" means, unless otherwise stated, a fluorine, chlorine, bromine, or iodine atom.

The term "haloalkyl" refers to alkyl moieties having a halogen replacing a hydrogen on one or more carbons of the hydrocarbon backbone. For example, the term "haloalkyl" includes trichloromethyl, trifluoromethyl, chloromethyl, chlorofluoromethyl, and the like.

Detection of Trace Anions

Provided herein are methods of detecting anions in solution. In particular, the methods described can be used to detect trace anions in a sample. For example, in some embodiments, the anions can be present in an amount of between about 500 femtomoles to about 10 millimoles. The methods described herein facilitate the detection of anions present at low concentrations and in the presence of high concentrations (e.g., 1 million times excess) of other background ions. These methods are particularly useful for samples of limited volume, where rapid and simultaneous identification and quantification of an anion is desired, for example, in the production of PET radiotracers and in the analysis of water contaminants.

The sensitivity of the method is such that it requires only a small fraction (<10%) of the $^{18}$O-labeled water target, and enables pre-screening of the $^{18}$F fluoride solution prior to radiotracer preparation. Since the target volume is normally on the order of one mL and the $^{18}$F-fluoride concentration is typically on the order of 1 nanomole/mL, the method is able to detect and quantify 1-2 ng of $^{18}$F-fluoride ion the presence of $^{19}$F-fluoride and other anionic contaminants. Moreover, the dynamic range is sufficient to quantify the $^{18}$F/$^{19}$F-fluoride ion ratio even in the presence of a large excess of $^{19}$F-fluoride ion.

In some embodiments, a method of detecting an anion, Y, can include combining a compound of formula (I):

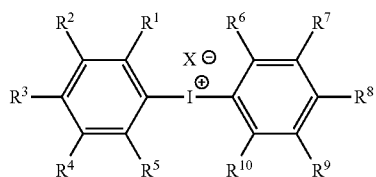

(I)

wherein:
$R^1$, $R^2$, $R^3$, $R^4$, $R^5$, $R^6$, $R^7$, $R^8$, $R^9$, $R^{10}$ are independently chosen from: H, —$(C_1$-$C_{10})$alkyl, —$(C_1$-$C_{10})$haloalkyl, $(C_2$-$C_{10})$alkenyl, $(C_2$-$C_{10})$alkynyl, —O—$(C_1$-$C_{10})$alkyl, halogen, —C=O—O—$(C_1$-$C_{10})$alkyl, aryl, and heteroaryl, or a linking group that is bound either covalently or noncovalently to a solid support; and
X is a weakly coordinating anion;
with a sample comprising one or more anions, Y, in a solvent, to prepare a compound of formula (II):

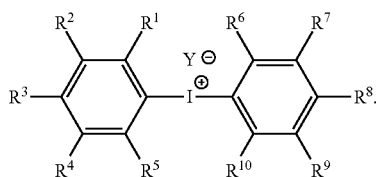

(II)

Decomposition of the compound of formula (II) can result in the formation of an aromatic compound of formula (III) and/or (IV):

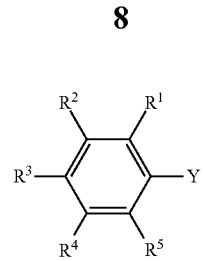

(III)

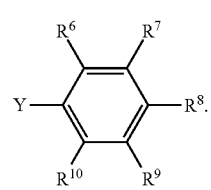

(IV)

As one of skill would recognize, the decomposition of the compound of formula (II) will also result in the formation of a corresponding aromatic compound of formula (V) and/or (VI):

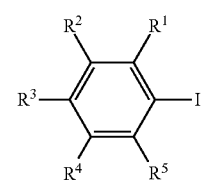

(V)

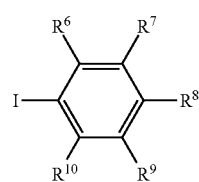

(VI)

The sample having a compound of formula (III) and/or (IV) can then be analyzed using mass spectroscopy to quantify the amount of the compound of formula (III) and/or (IV) present in the sample. The amount of these compounds can then be used to quantify the amount of anion Y. Those skilled in the art will recognize that substituents on the arene may be chosen to optimize the sensitivity of GC-MS or LC-MS detection schemes. Variables that may be readily tuned by substituents include ionization efficiency, column retention time, and reaction rate.

In some embodiments, the compound of formula (I) is chosen from:

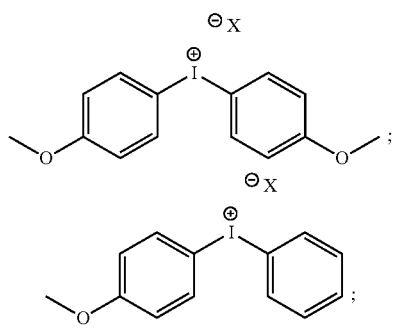

-continued

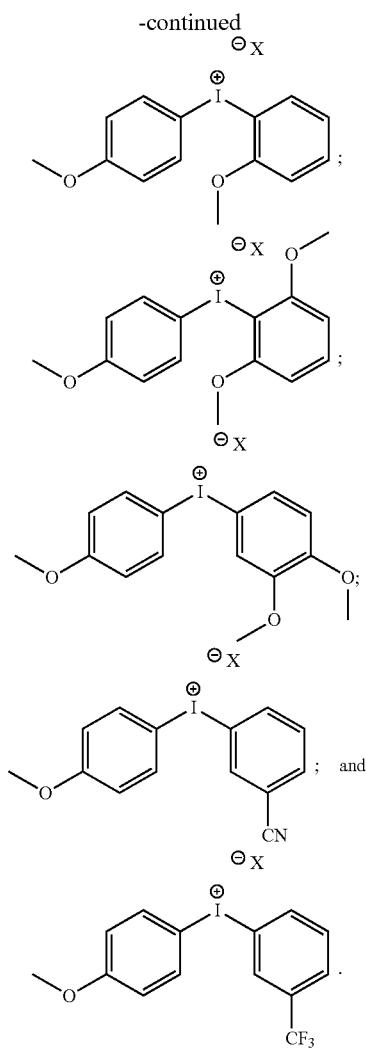

In some embodiments, the compound of formula (I) is:

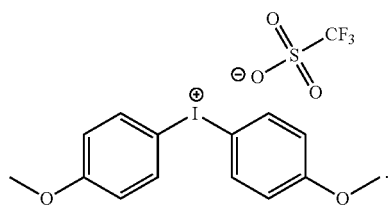

A weakly coordinating anion (X) (i.e., an anion that coordinates only weakly with iodine (III)) is generally the conjugate base of a strong acid, for example, any anion for which the pKa of the conjugate acid (H—X) is less than about 1. For example, X can be triflate, mesylate, nonaflate, hexaflate, toluene sulfonate, nitrophenyl sulfonate (nosylate), bromophenyl sulfonate (brosylate), tetraphenylborate, hexafluorophosphate, trifluoroacetate, tetrafluoroborate, or perchlorate.

An anion (Y) can include, for example, any anion for which the aqueous pKa of the conjugate acid (H—Y) is less than about 12 (e.g., less than about 10; less than about 8; less than about 5; less than about 3; less than about 1; less than zero; less than about −2; and less than about −5). For example, the anion can be a halide, aryl carboxylate, alkyl carboxylate, phosphate, phosphonate, phosphonite, azide, thiocyanate, cyanate, phenoxide, stabilized enolate, or mixture thereof. In some embodiments, Y can be fluoride, chloride, bromide, iodide, or azide. In some embodiments, Y is fluoride (e.g., a radioactive isotope of fluoride). In some embodiments, more than one Y is present. In some embodiments, when more than one Y is present, each Y is independently quantified or detected. In some embodiments, the pKa of H—Y is less than the pKa of H—X.

The methods described herein can be used when Y is present in the sample in an amount ranging from about 500 femtomoles to about 10 millimoles (e.g., about 500 femtomoles to about 5 millimoles; about 500 femtomoles to about 1 millimole; about 500 femtomoles to about 500 micromoles; about 500 femtomoles to about 100 micromoles; about 500 femtomoles to about 50 micromoles; about 500 femtomoles to about 5 micromoles; about 500 femtomoles to about 1 micromole; about 500 femtomoles to about 500 nanomoles; about 500 femtomoles to about 100 nanomoles; about 500 femtomoles to about 50 nanomoles; about 500 femtomoles to about 5 nanomoles; about 500 femtomoles to about 1 nanomole; about 1 picomoles to about 10 millimoles; about 100 picomoles to about 10 millimoles; about 500 picomoles to about 10 millimoles; about 1 nanomole to about 10 millimoles; about 50 nanomoles to about 10 millimoles; about 100 nanomoles to about 10 millimoles; about 500 nanomoles to about 10 millimoles; about 1 micromole to about 10 millimoles; about 50 micromoles to about 10 millimoles; about 100 micromoles to about 10 millimoles; about 500 micromoles to about 10 millimoles and about 1 millimole to about 10 millimoles). In some embodiments, Y is present in the sample in an amount of less than about 10 millimoles. In many cases, the compound of formula (I) is used in an excess when compared to the amount of Y present in the sample. In some embodiments, the sample of Y further contains additional compounds which may be present in an excess compared to Y. For example, the additional compounds may be present in more than one million fold excess compared to Y.

The solvent used in the solution comprising one or more Y can be a polar organic solvent, i.e. an organic solvent having a dielectric constant greater than about 10. In some embodiments, the polar solvent is a polar aprotic solvent, such as acetonitrile, acetone, dichloromethane, ethyl acetate, tetrahydrofuran, dimethylformamide, 1,2-difluorobenzene, benzotrifluoride, and mixtures thereof. In some embodiments, the polar aprotic solvent is acetonitrile. In some embodiments, the polar aprotic solvent has a boiling point that is less than about 90° C. (e.g., less than about 80° C.; less than about 70° C.; less than about 60° C.; less than about 55° C.; less than about 40° C.; less than about 35° C.; and less than about 30° C.) at 1 atmosphere.

In some embodiments, the method can further include removing the solvent following preparation of the compound of formula (II). The remaining sample (or residue) can then be dissolved in a nonpolar organic solvent and filtered prior to decomposition. A nonpolar organic solvent is an organic solvent having a dielectric constant of less than about 10. For example, benzene, toluene, o-xylene, diethyl ether, carbon tetrachloride, hexane, cyclohexane, fluorobenzene, chlorobenzene, nitrobenzene, and mixtures thereof. In some embodiments, the nonpolar organic solvent is benzene.

Decomposition of the compound of formula (II) can be accomplished by heating the sample at a temperature ranging from about 25° C. to about 250° C. (e.g., 25° C. to about 225° C.; 25° C. to about 200° C.; 25° C. to about 175° C.; 25° C. to about 150° C.; 25° C. to about 100° C.; 25° C. to about 75° C.;

25° C. to about 50° C.; 50° C. to about 250° C.; 75° C. to about 250° C.; 100° C. to about 250° C.; 125° C. to about 250° C.; 150° C. to about 250° C.; 175° C. to about 250° C.; 200° C. to about 250° C.; 50° C. to about 200° C.; and 75° C. to about 150° C.).

In some embodiments, the sample is heated from about 1 second to about 15 minutes (e.g., about 1 second to about 10 minutes; about 1 second to about 5 minutes; about 1 second to about 1 minute; about 1 second to about 30 seconds; about 1 second to about 10 seconds; about 5 seconds to about 15 minutes; about 30 seconds to about 15 minutes; about 1 minute to about 15 minutes; about 5 minutes to about 15 minutes; about 5 seconds to about 30 seconds; about 30 seconds to about 2 minutes; and about 5 minutes to about 10 minutes).

The heating can be accomplished by any reasonable means, including by a flash pyrolysis method, a conventional heating method, or by a microwave method. In some embodiments, decomposition can occur during direct injection of the sample into the hot injector port of the mass spectrometer (e.g., GC-MS). In some embodiments, decomposition of the compound of formula (II) is performed in the absence of solvent. In some embodiments, decomposition is performed under reduced pressure and/or in a sealed reaction vessel (e.g., a sealed NMR tube).

In some embodiments, the compound of Formula I is supported on a solid support by means of either a covalently bound linking group or by adsorption using noncovalent interactions. The solid support can take a number of different forms, including being porous or non-porous. Non-limiting examples of solid support materials include Teflon (poly(tetrafluoroethylene), silica gel functionalized with perfluoroalkylated silanes, polystyrene, polyacrylamide, nitrocellulose, agarose, glass, metal, and plastic. The solid support can also be transparent, translucent, opaque or reflective.

A covalently bound linking group can be any linking group that is not affected by the chemistry used to modify or extend the attached compound. The linker can facilitate the cleavage step by allowing cleavage to proceed readily and in a good yield. In some embodiments, the linker can provide attachment and cleavage of the compound from the solid support in quantitative yield. Non-limiting examples of such linkers include carboxylic acid linkers, carboxamide linkers, alcohol linkers, amine linkers, and traceless linkers.

Non-covalent adsorption can be used to anchor a compound of Formula I to the solid support through the formation of a range of noncovalent bonds between the solid support surface and the compound. In some embodiments, solid supports for this type of immobilization can include teflon or perfluoralkylated silica gel or other perfluoroalkylated metal oxide supports.

In some embodiments, noncovalent interactions between the compound of Formula I and the solid support can occur through a high affinity binding pair. As used herein, a "high affinity binding pair system" is a pair of reagents where a first member of the high affinity binding pair system binds to the second member of the high affinity binding pair system with a functional affinity (or avidity) sufficiently strong to allow stable aggregation of the compound and the support. A high affinity binding pair system typically exhibits an affinity between the first and second members of the high affinity binding pair of at least about $K\sim10^{-10}$. Suitable high affinity binding pairs include avidin and biotin, any protein that binds an immunoglobulin, and a ligand-receptor pair. Avidin includes avidin, modified avidin (such as deglycosylated avidin, neutravidin), streptavidin, and derivatives thereof, which bind biotin or its derivatives with high affinity. Proteins that bind an immunoglobulin include protein A, protein G, and protein L, and can be selected for their immunoglobulin specificity. Examples of ligand-receptor pairs that can serve as a high affinity binding pair include a small molecule and a macromolecule that binds the small molecule (for example, folic acid and a folate binding protein), and an antigen-antibody pair or hapten-antibody pair (for example, dinitrophenol, pyridoxal, or fluorescein and an appropriate anti-hapten antibody). The compound or the support can be linked to either the first or second member of a high affinity binding pair. The compound and the support may be independently linked to the member of the high affinity binding pair directly or through a linker.

In another embodiments, non-covalent interactions can implement a tagging strategy exploiting "fluorous" interactions. See for example, Curran, D. P. et al. Comb. Chem. 2000, 327-352. Fluorous phase extraction protocols using tagged biomolecules or reagents can be used to create slide-based microarrays of immobilized biomolecules. In some embodiments, a fluorous tagged ($C_nF_{(2n+1)}$) compound of interest can be immobilized (e.g., temporarily) on a fluorous support using a fluorophobic solvent such as acetonitrile, and all other reaction components can be washed away. For example, a simple $C_8F_{17}$ fluorous ponytails can be used to immobilize carbohydrates on glass slides coated with fluoroalkylsilanes. See, for example, Ko, K. S. et al., J. Am. Chem. Soc. 2005, 127, 13162-13163.

Without being bound by theory, given their generally inert nature, it most fluorous support materials will suffice for radiochemical applications. For example, powdered polyfluorinated resins (PTFE or PFA (DuPont)) or heavily fluorinated silica gels (FluoroFlash (Fluorous Technologies)) that can be sealed into HPLC columns are available commercially and can be used in this application.

As a non-limiting example, synthesis of a tagged diaryliodonium salts can proceed as follows.

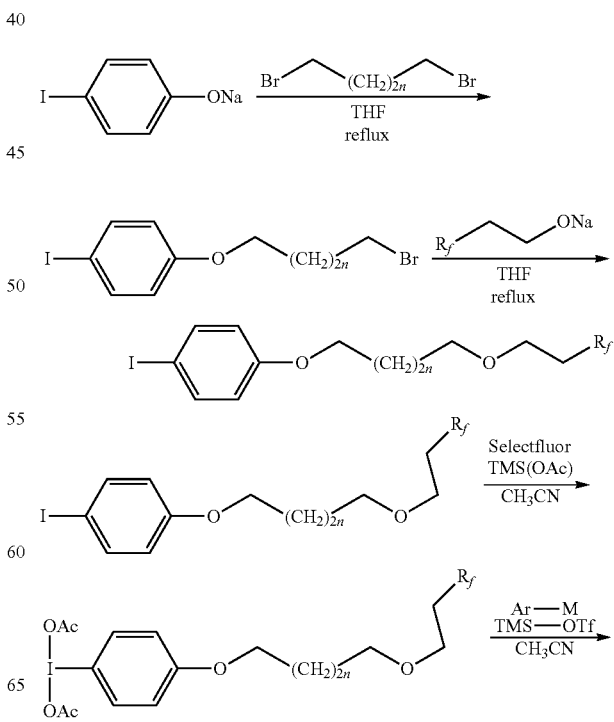

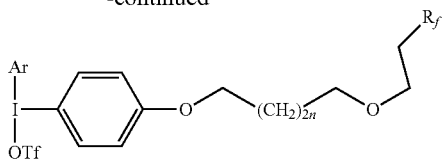

(n = 1, 2, 3)
Rf = C$_8$F$_{17}$, C$_{10}$F$_{19}$

Fluorous alcohols may be used as a fluorous tag based, in part on their ease of synthesis and the robustness of the ether linkage. It has been demonstrated that simple S$_N$2 reactions of fluorous tagged alkoxides with unactivated alkyl bromides can proceed in high yield in ethereal solvents, though phase transfer catalysts were necessary in some instances (Huang, W. et al., *Journal of Colloid and Interface Science* 2004, 272, 457-464). Oxidation of the tagged iodophenols or Pd-catalyzed formation of the corresponding arylstannanes will be performed as shown above. In some embodiments, as an alternative to the alkyl group connecting the diaryliodonium salt to the fluorous tag, other linkages can be used as well, including polyethylene glycol (PEG) ethers, or mixtures of aliphatic, aromatic, and PEG linkers. The length of the perfluoroalkyl chain (Rf in the scheme above) can range from C$_6$F$_{13}$ to C$_{20}$F$_{41}$. In addition, multiple fluorous tags may be incorporated into the same iodonium salt.

Analysis of the sample of compounds of formula (III) and/or (IV) can be performed using mass spectroscopy. Such methods can include, for example, gas chromatography-mass spectroscopy (GC-MS) and liquid chromatography-mass spectroscopy (LC-MS). In some embodiments, the analysis is performed using further processing techniques as known to those of skill in the art, such as ion-selected mass spectroscopy (see FIG. 1). The methods described herein can be used to determine the amount of Y present quantitatively. For example, the concentration and isotope ratio (e.g., the $^{18}$F:$^{19}$F isotope ratio) of anions (Y) can be determined quantitatively. In some embodiments, the presence or absence of Y (e.g., $^{18}$F) in a sample can be determined.

In some embodiments, the method can include combining a compound of formula (I), as described herein, with a sample comprising one or more anions, Y, in a polar organic solvent, to prepare a compound of formula (II), as described above. The polar organic solvent can then be removed and the remaining sample dissolved in a nonpolar organic solvent. This sample can then be decomposed to form an aromatic compound of formula (III) and/or (IV), as described above. The resulting sample can then be analyzed using mass spectroscopy to quantify the amount of the compound of formula (III) and/or (IV), thereby quantifying the amount of anion Y.

In some embodiments, the methods described herein can be used to identify and quantify background anion (Y) contaminants in water or other solvents. In some embodiments, the methods described herein can be used concurrently with the synthesis of a compound of interest (e.g., a PET imaging agent). For example, the assay can be run (e.g., for quality control to test for excessive amounts of background $^{19}$F fluoride in the cyclotron target) concurrently with radiotracer synthesis so that it does not delay production of PET imaging agents.

Kits

Also provided herein are kits. Typically, a kit includes a compound of formula (I), as described previously. In some embodiments, a kit includes compound of formula (I), and directions for use of the kit (e.g., instructions for analyzing a sample). In some embodiments, the kit can include a compound of formula (I) and a label that indicates that the contents are to be used to analyze a sample for the presence or absence of trace anions.

EXAMPLES

General Methods

Tetramethylammonium fluoride (TMAF, Aldrich) and diphenyliodonium nitrate were dried at 60-80° C. in a drying pistol (charged with P$_2$O$_5$) under dynamic vacuum for one week. Hexabutylditin and tributyltin chloride (Aldrich) were distilled into flame-dried storage tubes under dry nitrogen. Acetonitrile and acetonitrile-d$_3$ were refluxed with P$_2$O$_5$, benzene and benzene-d$_6$ with CaH$_2$, overnight and distilled directly into flame-dried storage tubes under dry nitrogen. All glassware, syringes, and NMR tubes were oven dried (140° C.) for more than 24 hours before they were transferred into the glovebox for use. All other reagents were purchased from commercial sources and were used as received. All NMR experiments were performed using a Bruker Avance 400 MHz NMR spectrometer.

Example 1

Preparation of p-methoxyphenyliodonium diacetate p-methoxyphenyliodonium diacetate: 2.34 g (10 mmol) p-iodoanisole was dissolved in 90 mL of glacial acetic acid. The solution was stirred, heated to 40° C. and 13.6 g (110 mmol) sodium perborate tetrahydrate was added in gradually in an hour. The reaction mixture was kept at 40° C. for 8 hours before being cooled to room temperature. Half of the acetic acid (~45 mL) was removed and 100 mL of deionized water was added. 3×40 mL dichloromethane was used to extract the aqueous solution. The combined organic layers were dried over sodium sulfate and solvent was evaporated to give 2.25 g (64%) of p-methoxyiodonium diacetate, which was dried in vacuo and used without further purification. o-methoxyphenyliodonium diacetate (65%), m-cyanophenyliodonium diacetate (70%), m-trifluoromethylphenyliodonium diacetate (80%), and 2,6-dimethoxyphenyliodoniu diacetate (83%) were synthesized using a similar procedure starting from the corresponding iodoarenes.

Example 2

Preparation of bis(p-methoxyphenyl)iodonium trifluoroacetate

Bis(p-methoxyphenyl)iodonium trifluoroacetate: Under N$_2$ protection, 1.41 g (4 mmol) p-methoxyphenyliodonium diacetate was dissolved in 30 mL of dry dichloromethane and the solution was cooled to -30° C. 0.61 mL (8 mmol) of trifluoroacetic acid was added and the solution was slowly brought back to room temperature and stirred at room temperature for 30 minutes. The solution was, again, cooled to -30° C. and 0.44 mL (4 mmol) anisole was added slowly and the mixture was warmed back up to room temperature and stirred for 1 hour. The solvent was evaporated and the residual solid was recrystallized from diethylether/dichloromethane to give 1.53 g bis(p-methoxyphenyl)iodonium trifluoroacetate (71%).

Example 3

Preparation of bis(p-methoxyphenyl)iodonium tosylate

Bis(p-methoxyphenyl)iodonium tosylate: Under N$_2$ protection, 352 mg (1 mmol) p-methoxyphenyliodonium diacetate was dissolved in 1.5 mL of dry acetonitrile. The solution was combined with a solution of 190 mg (1 mmol) tosylic acid monohydrate in 1.5 mL of dry acetonitrile. After addition of 0.11 mL (1 mmol) p-iodoanisole, the mixture was allowed to react at room temperature for 2 hours. The solvent was then removed and the remaining solid was recrystallized from diethylether/dichloromethane to give 422 mg bis(p-methoxyphenyl)iodonium tosylate (82%).

Example 4

Preparation of bis(p-methoxyphenyl)iodonium hexafluorophosphate

Bis(p-methoxyphenyl)iodonium hexafluorophosphate: Under $N_2$ protection, 352 mg (1 mmol) p-methoxyphenyliodonium diacetate was dissolved in 1.5 mL of dry acetonitrile. The solution was combined with a solution of 190 mg (1 mmol) tosylic acid monohydrate in 1.5 mL of dry acetonitrile. After addition of 0.11 mL (1 mmol) p-iodoanisole, the mixture was allowed to react at room temperature for 2 hours. 10 mL of water was added to the reaction mixture followed by extraction with 3×5 mL hexanes. The water layer was treated with 502 mg (3 mmol) $NaPF_6$. The white precipitation was taken up in dichloromethane and recrystallization with diethylether/dichloromethane gave 391 mg bis(p-methoxyphenyl) iodonium hexafluorophosphate (80.5%).

Example 5

Preparation of phenyl-4-methoxyphenyliodonium hexafluorophosphate

Phenyl-4-methoxyphenyliodonium hexafluorophosphate was synthesized according to the procedure described for the synthesis of bis(p-methoxyphenyl)iodonium hexafluorophosphate from the corresponding aryliodonium diacetate and anisole. (77.9%)

Example 6

Preparation of 2-methoxyphenyl-4'-methoxyphenyliodonium hexafluorophosphate 2-methoxyphenyl-4'-methoxyphenyliodonium hexafluorophosphate was synthesized according to the procedure described for the synthesis of bis(p-methoxyphenyl)iodonium hexafluorophosphate from the corresponding aryliodonium diacetate and anisole. (83.3%)

Example 7

Preparation of 3-cyanophenyl-4'-methoxyphenyliodonium hexafluorophosphate 3-cyanophenyl-4'-methoxyphenyliodonium hexafluorophosphate was synthesized according to the procedure described for the synthesis of bis(p-methoxyphenyl)iodonium hexafluorophosphate from the corresponding aryliodonium diacetate and anisole. (73.7%)

Example 8

Preparation of 3-(trifluoromethyl)phenyl-4'-methoxyphenyliodonium hexafluorophosphate 3-(trifluoromethyl)phenyl-4'-methoxyphenyliodonium hexafluorophosphate was synthesized according to the procedure described for the synthesis of bis(p-methoxyphenyl) iodonium hexafluorophosphate from the corresponding aryliodonium diacetate and anisole. (96.1%)

Example 9

Preparation of 2,6-dimethoxyphenyl-4'-methoxyphenyliodonium hexafluorophosphate 2,6-dimethoxyphenyl-4'-methoxyphenyliodonium hexafluorophosphate was synthesized according to the procedure described for the synthesis of bis(p-methoxyphenyl) iodonium hexafluorophosphate from the corresponding aryliodonium diacetate and anisole. (86%)

Example 10

Preparation of 2-Bromo-4,5-dimethoxylbenzeneethanamine

2-Bromo-4,5-dimethoxylbenzeneethanamine: Bromine (1.1 mL, 22 mmol) in acetic acid (10 mL) was slowly added into a vigorously stirred solution of 2-(3,4-dimethoxyphenyl) ethylamine (3.4 mL, 20 mmol) in 50 mL acetic acid. 2-bromo-4,5-dimethoxylbenzeneethanamine started to precipitate after 15 minutes. The mixture was stirred for another two hours, filtered, and washed with dichloromethane 10 mL×3 and petroleum ether 10 mL×3. The resulting solid was taken up in water and the pH was brought to 10 with aqueous KOH solution. Extraction with dichloromethane followed by evaporation of the solvent yielded 4.12 g (78%) 2-Bromo-4, 5-dimethoxylbenzeneethanamine. The crude product was dried under dynamic vacuum overnight and used without further purification.

Example 11

Preparation of 2-Bromo-4,5-dimethoxyl-(2-phthalimidoethyl)benzene

2-Bromo-4,5-dimethoxyl-(2-phthalimidoethyl)benzene: 2-Bromo-4,5-dimethoxylbenzeneethanamine (3.5 g 13.2 mmol) was dissolved and stirred in 50 mL dry acetonitrile. 2.14 mL (1.1 equiv) phthaloyl dichloride and 7 mL (3 equiv) Hünig's base were added. The mixture was stirred at room temperature overnight. Acetonitrile was removed; the remaining product was taken up in dichloromethane and washed with basic water (pH=11). The aqueous wash was extracted with dichloromethane 15 mL×3. The organic fractions were combined and dried over sodium sulfate. Solvent was removed to give the crude product, which was then purified by column chromatography. Calculated yield: 1.8 g (34%).

Example 12

Preparation of 3,4-dimethoxyphenyltributyltin 3,4-dimethoxyphenyltributyltin: Under $N_2$ protection, 1.085 g (5 mmol) 4-bromoveratrole and 289 mg (5 mol %) $Pd(0)(PPh_3)_4$ was dissolved in 15 mL of dry toluene, the solution was transferred into a storage tube equipped with teflon chemcap seal, 3.19 g (5 mmol) hexabutylditin was added. The tube was sealed, heated to, and kept at 120° C. for 48 hours. The reaction mixture was allowed to cool to room temperature and diluted with 15 mL of hexane. 15 mL of saturated aqueous KF solution was added and the mixture was stirred for 30 minutes followed by filtration through celite. The organic layer was separated, and the solvent was removed to give the crude product as a yellow oil. The crude product was purified by column chromatography (hexane/dichloromethane 98/2, basic alumina) to give 1.69 g (79.1%) pure 3,4-dimethoxyphenyltributyltin.

Example 13

Preparation of 3,4-dimethoxy-2-methylphenyltributyltin 3,4-dimethoxy-2-methylphenyltributyltin was synthesized in a similar fashion as described in the procedure for the synthesis of 3,4-dimethoxyphenyltributyltin from the corresponding brominated precursor. (76.2%)

Example 14

Preparation of 3,4-dimethoxy-2-(2-phthalimido)phenyltributyltin 3,4-dimethoxy-2-(2-phthalimido)phenyltributyltin was synthesized in a similar fashion as described in the procedure for the synthesis of 3,4-dimethoxyphenyltributyltin from the corresponding brominated precursor. (20%)

Example 15

3,4-dimethoxyphenyl-4'-methoxyphenyliodonium hexafluorophosphate 3,4-dimethoxyphenyl-4'-methoxyphenyliodonium hexafluorophosphate: Under $N_2$ protection, 352 mg (1 mmol) p-methoxyphenyliodonium diacetate was dissolved in 1.5 mL of dry acetonitrile. The solution was combined with a solution of 190 mg (1 mmol) tosylic acid monohydrate in 1.5 mL of dry acetonitrile. After addition of 427 mg (1 mmol) 3,4-dimethoxyphenyltributyltin, the mixture was allowed to react at room temperature for 2 hours. 10 mL of water was added to the reaction mixture followed by extraction with 3×5 mL hexanes. The water layer was treated with 502 mg (3 mmol) $NaPF_6$. The white precipitate was taken up in dichloromethane and recrystallization with diethylether/dichloromethane gave 370 mg (71.7%) 3,4-dimethoxyphenyl-4'-methoxyphenyliodonium hexafluorophosphate.

Example 16

Preparation of 3,4-dimethoxy-2-methylphenyl-4'-methoxyphenyliodonium hexafluorophosphate 3,4-dimethoxy-2-methylphenyl-4'-methoxyphenyliodonium hexafluorophosphate was synthesized in a similar fashion as 3,4-dimethoxyphenyl-4'-methoxyphenyliodonium hexafluorophosphate from p-methoxyphenyliodonium diacetate and the corresponding aryl tin precursor. (75%)

Example 17

Preparation of 3,4-dimethoxy-2-(2-phthalimidoethyl) phenyl-4'-methoxyphenyliodonium hexafluorophosphate 3,4-dimethoxy-2-(2-phthalimidoethyl)phenyl-4'-methoxyphenyliodonium hexafluorophosphate hexafluorophosphate was synthesized in a similar fashion as 3,4-dimethoxyphenyl-4'-methoxyphenyliodonium hexafluorophosphate from p-methoxyphenyliodonium diacetate and the corresponding aryl tin precursor. (55%)

Example 18

Detection of Trace Fluoride

Figure 2:
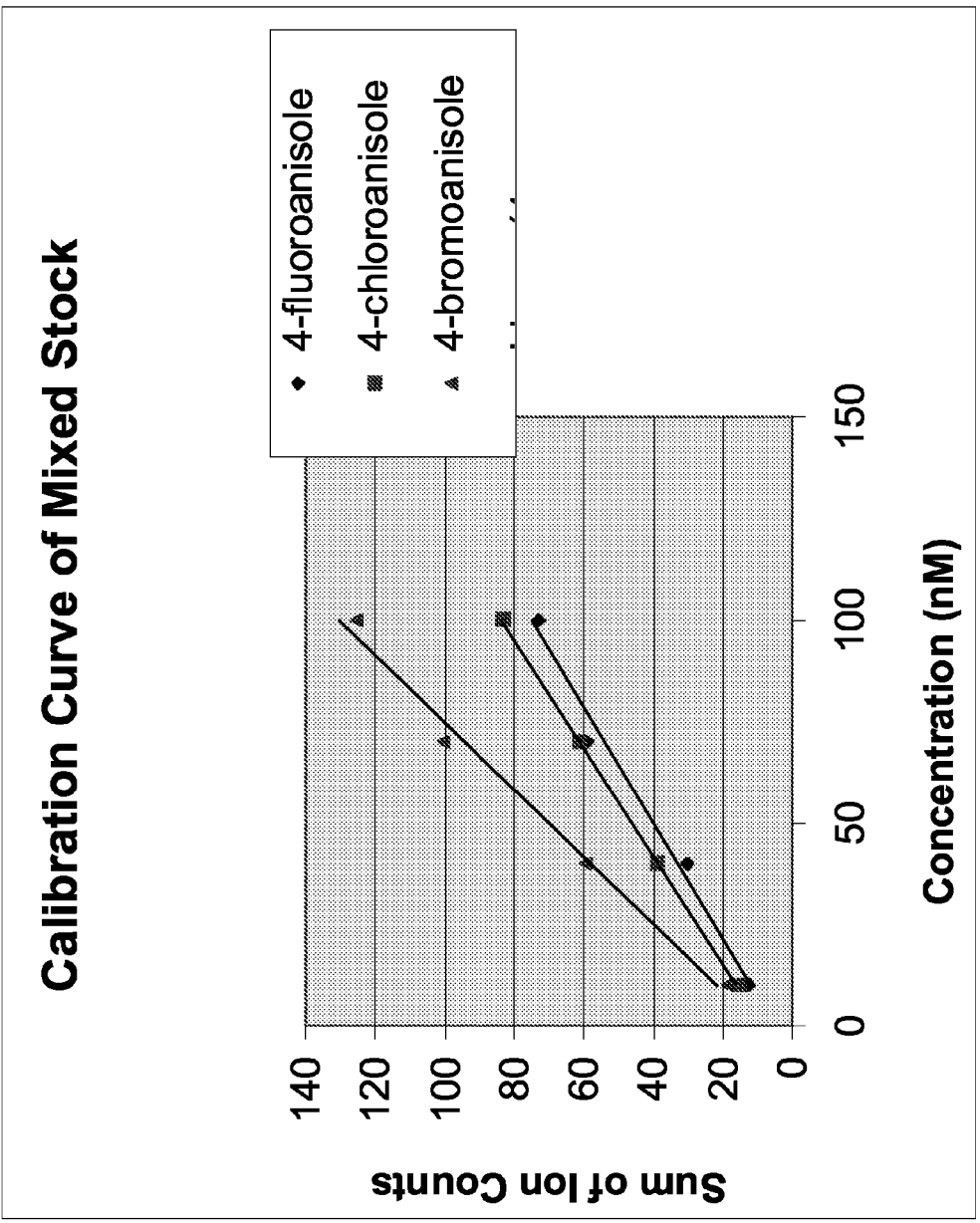
FIG. 2 is a standard concentration curve for 4-fluoroanisole.

A mixture containing 5 ng of tetramethylammonium fluoride and 1 mg of bis(4-methoxypheny)iodonium trifluoroacetate was dissolved in 0.5 mL of benzene and heated to 140° C. for 15 minutes. A 5 µL aliquot of this sample was injected directly into the injector port (250° C., 5:1 split) of a Waters GC-T GC-MS equipped with a JW Scientific (122-5532) DB5-MS (30 meters×0.25 mm) gas chromatography column to record the spectra shown in FIG. 1. The concentration of 4-fluoroanisole produced was determined by comparison to a standard curve (FIG. 2). The transfer of fluoride to the arene under these conditions was typically 85±10%.

Example 19

Detection of Trace Fluoride

A mixture containing 5 ng of tetramethylammonium fluoride and 1 mg of bis(4-methoxypheny)iodonium trifluoroacetate was dissolved in 0.5 mL of acetonitrile. The solvent was removed at room temperature under reduced pressure. The remaining solid was treated with benzene (0.5 mL) and a 5 µL aliquot of this solution was injected directly into the injector port (250° C., 5:1 split) of a Waters GC-T GC-MS equipped with a JW Scientific (122-5532) DB5-MS (30 meters×0.25 mm) gas chromatography column. The concentration of 4-fluoroanisole produced was determined by comparison to a standard curve (see FIG. 2). The transfer of fluoride to the arene under these conditions was typically 80±10%.

A number of embodiments of the invention have been described. Nevertheless, it will be understood that various modifications may be made without departing from the spirit and scope of the invention. Accordingly, other embodiments are within the scope of the following claims.

What is claimed is:
1. A method of quantifying the amount of one or more anions, Y, in a sample, the method comprising:
(a) combining a compound of formula (I):

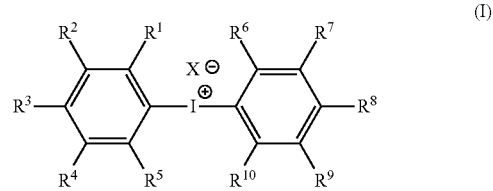

wherein:
$R^1$, $R^2$, $R^3$, $R^4$, $R^5$, $R^6$, $R^7$, $R^8$, $R^9$, $R^{10}$ are independently chosen from: H, —($C_1$-$C_{10}$)alkyl, —($C_1$-$C_{10}$)haloalkyl, ($C_2$-$C_{10}$)alkenyl, ($C_2$-$C_{10}$)alkynyl, —O—($C_1$-$C_{10}$) alkyl, halogen, —C=O—O—($C_1$-$C_{10}$)alkyl, aryl, and heteroaryl, or a linking group that is bound either covalently or noncovalently to a solid support; and
X is a weakly coordinating anion;
with a sample comprising one or more anions, Y, in a solvent, to prepare a compound of formula (II):

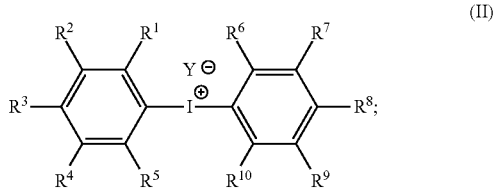

(b) decomposing the compound of formula (II) to form an aromatic compound of formula (III) and/or (IV):

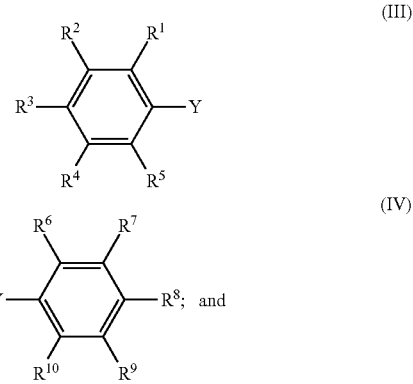

(c) analyzing the sample using mass spectroscopy to quantify the amount of the compound of formula (III) and/or (IV), thereby quantifying the amount of anion Y.

2. The method of claim 1, wherein the compound of formula (I) is:

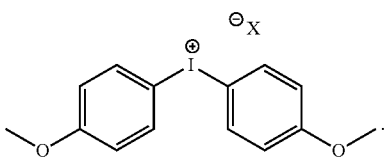

3. The method of claim 1, wherein the compound of formula (I) is in excess compared to Y.

4. The method of claim 1, wherein X is chosen from: triflate, mesylate, nonaflate, hexaflate, toluene sulfonate, nitrophenyl sulfonate, bromophenyl sulfonate, tetraphenylborate, hexafluorophosphate, trifluoroacetate, tetrafluoroborate, and perchlorate.

5. The method of claim 1, wherein the solvent is a polar organic solvent.

6. The method of claim 5, wherein the method further comprises:
(a2) removing the polar organic solvent; and
(a3) dissolving the remaining sample in a nonpolar organic solvent prior to decomposing.

7. The method of claim 6, wherein the nonpolar organic solvent is chosen from: benzene, toluene, o-xylene, diethyl ether, carbon tetrachloride, hexane, cyclohexane, fluorobenzene, chlorobenzene, nitrobenzene, and mixtures thereof.

8. The method of claim 5, wherein the method further comprises:
(a2) removing the polar organic solvent;
(a3) dissolving the remaining sample in a nonpolar organic solvent; and
(a4) removing residual salt by filtration prior to decomposing.

9. The method of claim 5, wherein the polar organic solvent is chosen from: acetonitrile, acetone, dichloromethane, ethyl acetate, tetrahydrofuran, dimethylformamide, 1,2-difluorobenzene, benzotrifluoride and mixtures thereof.

10. The method of claim 1, wherein the decomposing comprises heating the sample at a temperature ranging from about 25° C. to about 250° C.

11. The method of claim 10, wherein the sample is heated from about 1 second to about 15 minutes.

12. The method of claim 10, wherein the heating is accomplished by a flash pyrolysis method, a conventional heating method, or by a microwave method.

13. The method of claim 1, wherein the pKa of the conjugate acid of Y is less than 12.

14. The method of claim 13, wherein Y is chosen from: halide, aryl carboxylate, alkyl carboxylate, phosphate, phosphonate, phosphonite, azide, thiocyanate, cyanate, phenoxide, and mixtures thereof.

15. The method of claim 1, wherein Y is chosen from: fluoride, chloride, bromide, iodide, and azide.

16. The method of claim 15, wherein Y is fluoride.

17. The method of claim 1, wherein Y is a radioactive isotope of fluoride.

18. The method of claim 1, wherein Y is present in the sample in an amount from about 500 femtomoles to about 10 millimoles.

19. The method of claim 18, wherein the anion is present in the sample in an amount from about 500 femtomoles to about 1 millimole.

20. The method of claim 19, wherein the anion is present in the sample in an amount from about 500 femtomoles to about 1 micromole.

21. The method of claim 20, wherein the anion is present in the sample in an amount from about 500 femtomoles to about 1 nanomole.

22. The method of claim 1, wherein the anion is present in the sample in an amount of less than about 10 millimoles.

23. The method of claim 1, wherein the analyzing includes determining the amount of Y quantitatively.

24. The method of claim 1, wherein the analyzing includes determining the concentration of Y quantitatively.

25. The method of claim 1, wherein the analyzing includes determining the isotope ratio of Y.

26. The method of claim 25, wherein the isotope ratio is the $^{18}F:^{19}F$ isotope ratio.

27. The method of claim 1, wherein the compound of formula (II) is decomposed in the absence of solvent.

28. A method of quantifying the amount of one or more anions, Y, in a sample, the method comprising:
(a) combining a compound of formula (I):

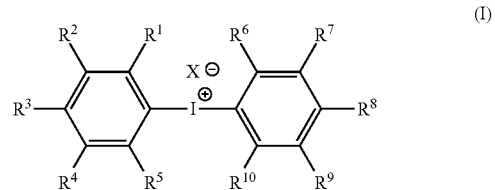

wherein:
R$^1$, R$^2$, R$^3$, R$^4$, R$^5$, R$^6$, R$^7$, R$^8$, R$^9$, R$^{10}$ are independently chosen from: H, —(C$_1$-C$_{10}$)alkyl, —(C$_1$-C$_{10}$)haloalkyl, (C$_2$-C$_{10}$)alkenyl, (C$_2$-C$_{10}$)alkynyl, —O—(C$_1$-C$_{10}$)alkyl, halogen, —C=O—O—(C$_1$-C$_{10}$) alkyl, aryl, and heteroaryl, or a linking group that is bound either covalently or noncovalently to a solid support; and X is a weakly coordinating anion;

with a sample comprising one or more anions, Y, in a polar organic solvent, to prepare a compound of formula (II):

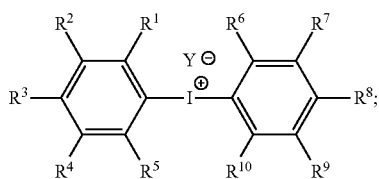
(II)

(b) removing the polar organic solvent;
(c) dissolving the remaining sample in a nonpolar organic solvent;
(d) decomposing the compound of formula (II) to form an aromatic compound of formula (III) and/or (IV):

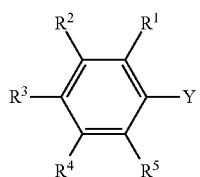
(III)

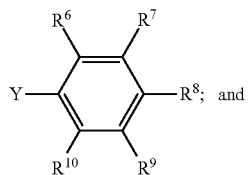
(IV)

(e) analyzing the sample using mass spectroscopy to quantify the amount of the compound of formula (III) and/or (IV), thereby quantifying the amount of anion Y.

29. A method of determining the presence or absence of one or more anions, Y, in a sample, the method comprising:
(a) combining a sample with a compound of formula (I):

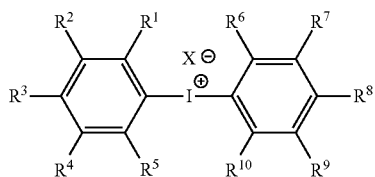
(I)

wherein:
R$^1$, R$^2$, R$^3$, R$^4$, R$^5$, R$^6$, R$^7$, R$^8$, R$^9$, R$^{10}$ are independently chosen from: H, —(C$_1$-C$_{10}$)alkyl, —(C$_1$-C$_{10}$)haloalkyl, (C$_2$-C$_{10}$)alkenyl, (C$_2$-C$_{10}$)alkynyl, —O—(C$_1$-C$_{10}$)alkyl, halogen, —C=O—O—(C$_1$-C$_{10}$) alkyl, aryl, and heteroaryl, or a linking group that is bound either covalently or noncovalently to a solid support; and X is a weakly coordinating anion; and
(b) analyzing the sample for the presence or absence of one or more anions, Y, using mass spectroscopy.

\* \* \* \* \*